United States Patent [19]
Woo

[11] Patent Number: 5,529,569
[45] Date of Patent: Jun. 25, 1996

[54] TREATMENT OF AILMENTS, AFFLECTIONS AND DISEASES

[76] Inventor: Gilson Woo, 15576 Lujon St., Hacienda Heights, Calif. 91745

[21] Appl. No.: 370,566

[22] Filed: Jan. 9, 1995

Related U.S. Application Data

[63] Continuation of Ser. No. 206,194, Mar. 3, 1994, abandoned, which is a continuation of Ser. No. 87,026, Jul. 2, 1993, abandoned, which is a continuation of Ser. No. 999,679, Dec. 31, 1992, abandoned, which is a continuation of Ser. No. 850,220, Mar. 12, 1992, abandoned, which is a continuation of Ser. No. 593,263, Oct. 1, 1990, abandoned, which is a continuation of Ser. No. 427,898, Oct. 24, 1989, abandoned, which is a continuation of Ser. No. 274,727, Nov. 10, 1988, abandoned, which is a continuation of Ser. No. 93,964, Sep. 8, 1987, abandoned.

[51] Int. Cl.$^6$ ...................................................... A61N 2/08
[52] U.S. Cl. ................................................ 600/9; 128/898
[58] Field of Search ............................. 600/9, 11, 13–15; 128/898

[56] References Cited

U.S. PATENT DOCUMENTS

| 1,006,415 | 10/1911 | Stubling et al. | 600/15 |
| 3,921,620 | 11/1975 | Nakayama | 128/1.3 |
| 4,134,395 | 1/1979 | Davis | 600/9 |
| 4,587,956 | 5/1986 | Griffin et al. | 128/1.3 |

FOREIGN PATENT DOCUMENTS

| 0100050 | 2/1984 | European Pat. Off. | 600/15 |
| 0199872 | 11/1986 | European Pat. Off. | 128/1.3 |
| 2575926 | 7/1986 | France | 600/15 |
| 3246128 | 6/1983 | Germany | 128/1.3 |
| 0891099 | 12/1981 | U.S.S.R. | 600/9 |
| 1204211 | 1/1986 | U.S.S.R. | 600/9 |
| 1323222 | 7/1973 | United Kingdom | 128/1.3 |
| 2168898 | 7/1986 | United Kingdom | 600/9 |

OTHER PUBLICATIONS

Mansfield, P. et al., "NMR Imaging in Biomedicine," Academic Press, NY, NY, © 1982, pp. 297–332.

*Primary Examiner*—Krista M. Zele
*Attorney, Agent, or Firm*—Irving Kischner

[57] ABSTRACT

A method and apparatus for alleviating or curing human ailments, afflictions and diseases by application of magnetism. A north pole surface of a magnet is applied to the hands or at least one hand of a person being treated, and is maintained in contact for a time period or periods in accordance with the ailments or afflictions being treated. The magnet is maintained in contact for a time period or periods sufficient to elicit affirmative response, alleviation, or cure. Concurrently with application of the magnet to the hands, an additional magnet or magnets may be applied to a particular afflicted area or areas of the body of the person, the additional magnet or magnets being configured to accommodate the area being treated and having appropriate total magnetic flux.

12 Claims, 1 Drawing Sheet

TREATMENT OF AILMENTS, AFFLICTIONS AND DISEASES

This application is a continuation of Ser. No. 08/206,194 filed Mar. 3, 1994, now abandoned, which is a continuation of Ser. No. 08/087,026, filed Jul. 2, 1993, now abandoned, which is a continuation of Ser. No. 07/999,679 filed Dec. 31, 1992, now abandoned, which is a continuation of Ser. No. 07/850,220, filed Mar. 12, 1992, now abandoned, which is a continuation of Ser. No. 07/593,263 filed Oct. 1, 1990, now abandoned, which is a continuation of Ser. No. 07/427,898, filed Oct. 24, 1989, now abandoned, which is a continuation of Ser. No. 07/274,727 filed Nov. 10, 1988, now abandoned, which is a continuation of Ser. No. 07/093,964, filed Sep. 8, 1987, now abandoned.

BACKGROUND OF THE INVENTION

Magnets and magnetism have heretofore been utilized in the treating of human diseases and afflictions. This has been primarily an Oriental practice.

In such prior practice, relatively small, weak magnets have been utilized, and these have been applied to afflicted areas or points of ailment in direct applications in the effort to achieve alleviation or cure.

Prior Oriental practice and utilization of magnets in treatment of afflictions and diseases, including utilization of meridians, acupuncture points and techniques involving magnets, are set forth in Korean books identified as follows: *A Colored Topography of Acupuncture Meridians and Acupuncture Points,* by Yong Tae Choe and Soo Ho Lee, Kyung Hee University, Seoul, Korea, published by Ko Moon Sa, 1974; *Magnetic Therapy,* by Lee Byong-Guk and Kim Nam-Sop, published by Ge Chuk Mun Hwa Sa, 1983, Seoul, Korea; and *Magnetic Therapy Study,* by Yu Tae-u, published by Umyang Mag Jin Sa, 1979, Seoul, Korea.

In the prior art practice and utilization of magnets in efforts to effect cures, small magnets have generally been applied to afflicted points or areas, and relatively small magnets of relatively low strength have been utilized at afflicted areas or at meridian lines.

Magnets of relatively low strength have been applied at acupuncture points, and often negative and bad side effects and/or adverse reactions have resulted.

The shortcomings and defects of prior art methods, including their lack of effectiveness and side effect problems, have resulted in their not being widespread and popular.

In conventional or prior art methods of magnetic treatment, relatively small magnets, with only relatively weak strength, have generally been utilized. Typically, magnets of ⅛ inch of ¾ inch diameter have been utilized with 100 to 3,000 gauss. Such magnets have been applied at meridian points and ailment points. Acupuncture techniques utilizing magnets, as is well known, are relatively complicated and difficult to learn. In such prior methods, the diagnosis and treatment are much the same or like those practiced in accordance with acupuncture techniques, except that magnets are utilized instead of needles.

Undesirable side effects have been produced by such prior art techniques, particularly if not utilized properly with accurate meridian diagnosis. Such techniques have been found to be less effective than they purport to be. Such techniques require expert or professional knowledge of Oriental medicine and/or acupuncture. They provide no means for treating a plurality of different ailments or diseases of a patient concurrently.

It is therefore an object of the invention to provide treatment for a wide variety of ailments and diseases, except for those requiring surgical treatment.

An object of the invention is to provide such treatment utilizing magnetism in simplified methods which can be practiced without specialized professional knowledge.

It is an object of the present invention to provide such a method which utilizes magnetism applied to the hands or a hand of a person, thus to provide concurrent treatment of a plurality of ailments and afflictions of the entire body.

An object of the invention is to provide such methods wherein magnetism is applied directly to afflicted areas of the body, concurrently with said application to the hands.

An object of the invention is to provide such methods which provide recovery from fatigue, which aid digestion and which relieve ill-feelings.

An object of the invention is the provision of such methods wherein the alleviative and curative effects are increased with increase of magnetic power or total flux to the person to the extent the person can tolerate and withstand such total flux.

An object of the invention is to provide such methods which provide substantial cures, relief of pain and rapid healing.

An object of the invention is to provide such methods which provide breathing control and/or improved circulation of the blood of the person.

It is an object of the invention to provide methods and techniques of treatment utilizing magnetism, independently of meridians or acupuncture points according to Oriental medicine.

An object of the invention is to provide such methods which may be applied for substantial periods and relatively continuously, without adverse reactions or side effects.

An object of the invention is the provision of such a method which is economical and effective.

An object of the invention is the provision of such a method which requires no additional treatment, equipment or drug.

An object of the invention is the provision of sucy methods which, properly utilized, are safe and involve no harm to a patient and no adverse reaction.

An object of the invention is the provision of such methods which involve the effecting of a balance of the systems of the body, in accordance with Oriental medicine theories, in treating ailments and applications.

SUMMARY OF THE INVENTION

The foregoing objects and advantages, as well as others which will be apparent from the specification, are achieved by a method for treating and alleviating human ailments, afflictions, and diseases by the application of magnetism to a person being treated. A north pole surface of a magnet is applied to the person, preferably to the hands or at least one hand. Contact with the magnet is maintained for a sufficient time period or periods to provide substantial alleviation or cure. The magnetic strength or total flux applied to the hands may typically be from about 5,000 to about 250,000 total flux. The magnet may be maintained in contact with the person for a time period sufficient for the eliciting of affirmative response, substantial alleviation or cure. In addition to application of magnetism to the hands, magnetism may concurrently be applied to a particular afflicted area or portion of the body of the person.

Magnet means are provided for application to the hands or other portions of the body of a person being treated, with a north pole surface of the magnet means configured to engage the portion or area of the person's body.

DESCRIPTION OF THE PREFERRED EMBODIMENT

Figure 1:
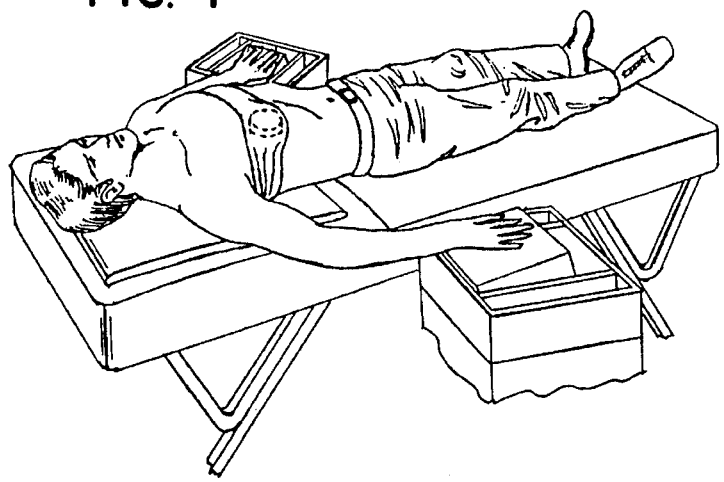
FIG. 1 is a perspective view showing a preferred manner of utilizing the invention in the application of magnet means to the hands of a person, with the person in a prone position.

The methods of treatment according to the invention include an indirect method wherein a magnet or magnets are applied to a hand or hands, and a combined method wherein, in addition to and concurrently with the indirect method, one or more magnets, are applied directly to one or more afflicted or ailing areas of the body of the person being treated.

The indirect method is the most effective and powerful method of treatment. In this method, magnets are applied to the palm or back side of the hands of a patient. Magnets are preferably applied to both hands at the same time, as shown in FIGS. 1, 2, 4 and 5 of the drawing. The magnets are preferably configured and sized to cover substantially the area of the hand, and preferably to cover the entire hand of the patient, including the fingers. Only the north pole of a magnet is applied for the reason that application of the south pole to the hand or other area of the body can produce negative results and undesirable or adverse side effects.

The afflictions, ailments and diseases of the entire body of a person may be treated concurrently by application of magnet means to the hands of the person.

In utilizing the indirect method in application to both hands of a patient, it is typically and ordinarily not necessary to utilize the direct method, unless it is appropriate or necessary to provide increased or added magnetic power or total flux for more effective treatment or to achieve full treatment or cure. Such addition of direct treatment to the indirect treatment might be appropriate in applying the additional magnetic power directly to an afflicted area for such afflictions as trauma, bruises, wounds, severe pains, sprain, and chronic diseases such as arthritis or continuous local pain.

The indirect method is believed to improve or effect a balance of the systems of the body in accordance with Oriental medical theory, wherein the condition and health of the human body is closely associated with overall balance of the systems of the body. Such balance or balance treatment is provided by the proper utilization of the indirect or hand method of treatment with strong magnets applied to both hands, balance treatment and balance are approached or achieved. Where only one hand is treated with magnetism, the hands should be treated alternatively, in order to avoid imbalance. For example, periods of treatment could alternate commencing with the left palm, then the back of the left hand, then the right palm, then the back of the right hand. Treatment could commence with application to the back of the right hand, then the right palm, then the back of the left hand, then the left palm. With concurrent treatment of both hands, the period of treatment would alternate between the palms of both hands and the backs of both hands. Without such alternation an unbalanced condition of the body systems can arise with resultant side effects and possible other illness.

The indirect method is applicable for all ailments, afflictions and diseases. As stated, it is the best and most effective method according to the invention, and serves to treat concurrently various or all afflictions and ailments of the entire body of a person.

The method also serves to relax the person, relieve tiredness and to tranquilize the person's nerves.

The direct method, in accordance with the invention, is utilized concurrently with the indirect method when appropriate and needed for treatment of particular afflicted areas, although in most cases, use of the direct method is unnecessary when the indirect method is utilized with magnets of sufficient strength and for proper periods of time.

Permanent magnets or electromagnets may be utilized in practicing the methods according to the invention. An electromagnet is provided which is sized and configured to cover substantially the area of the hand to be treated, and preferably to cover the entire hand, or for use in the direct method, the electromagnet is sized to accommodate the afflicted area of the body. Electromagnets have the advantage of being adjustable in and during use to provide a desired or needed level of power or gauss with appropriate electromagnet design. Permanent magnets have the disadvantage of being of fixed power. That is, any one magnet has a fixed total power or gauss level.

Treatment may begin with a relatively low power magnet, with successive application of magnets of increasing strength in accordance with the response and feeling of the patient relative to relief. Typically, response is felt after thirty minutes to one hour, and within two hours the patient can sense a cure in progress and has a good feeling. One to three hours of application is the optimum period for most effective treatment of most ailments or diseases. The magnet might be removed after such application.

Preferably, the person being treated should be in a prone position, as indicated in FIG. 1, during application of magnet means, because of the duration of treatment and the need for the person to be in a comfortable position to minimize tiring and to enable the person better to endure the treatment for the time period required.

Figure 2:
FIG. 2 is a perspective view showing the application of both hands of a person to magnet means.
Figure 3:
FIG. 3 is a perspective view of a person undergoing application of magnet means to both hands and the concurrent application of additional magnet means to a particular afflicted area of the back of the person.
Figure 4:
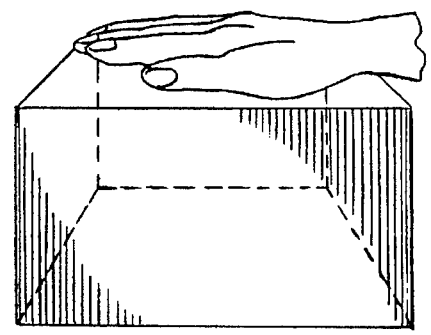
FIG. 4 is a perspective view showing the application of the hand of a person to the north pole surface of a magnet of rectangular configuration.
Figure 5:
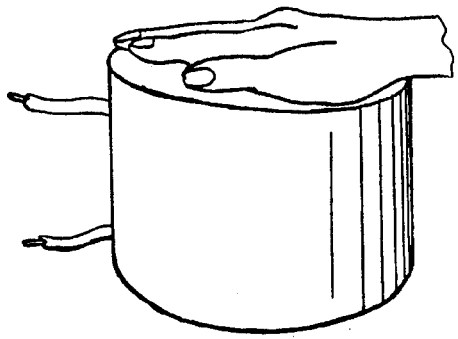
FIG. 5 is a perspective view showing the application of the hand of a person to a north surface of a magnet of generally oval cross-sectional configuration.

The hands may be applied to magnet means while the person is in a standing or sitting position, as indicated in FIGS. 2 and 3.

The treatment may be repeated at intervals in accordance with need and progress. For, relatively serious or long-term ailments, treatment may extend for many days, and even for a few months.

During indirect method treatment, the ailments, diseases and afflictions of a person are detected and sensed by the responses and symptoms of the person in response to the application of the magnetism. The cure in progress is sensed by the person during the application of magnetism in accordance with the invention. The response or reaction of the patient to the "indirect" treatment may involve the entire body. Symptoms occur from all diseased or afflicted areas of the body of the patient., and treatment is usually continued until all ailments and diseases are greatly alleviated or cured. The nature of the responses or reactions of a patient are difficult of definition, because the symptoms, reactions and responses may be subtle, delicate, and unique to the particular ailment and patient.

In utilizing the combined method, where chronic or serious disease is treated, first the hands are subjected to the magnetic indirect treatment according to the invention. Then, as indicated in FIG. 3 the direct treatment is employed by applying an appropriate magnet to the afflicted or pain area or spot, thus to increase the curing effects. The magnets may be applied as long as needed to produce desired results, and the patient can be treated for substantially unlimited time periods, so long as the patient does not tire and can withstand the treatment. This can be done without side effects or adverse reactions. However, if maintained in position for too long a time, a patient may become hungry or tired from the effects of treatment, as a result of improved digestion and beneficial effects of treatment according to the invention. Therefore, the following schedule may preferably be observed, in indirect and direct treatment:
Treatment: 2–3 hours
Resting time: 3–5 hours
Frequency: 2–4 times daily A magnet applied to a hand or to an afflicted area must be maintained in continuous contact during a specified treatment period. Otherwise, the treatment time prior to removal from contact is very likely to be ineffective and must be repeated.

For internal illnesses or ailments or chronic diseases, after twenty to forty-five minutes of application of the magnets under the indirect treatment, a response or reaction occurs in the patient, and the patient can sense a good response and active curing in one to two hours of treatment. After approximately two hours of application of the magnet, the response or reaction of the person's body gradually diminishes, the patient's body becomes relaxed, and a feeling of well-being permeates the patient's body.

Typically, the time of combined method treatment may extend from about one to four hours, and two to four times daily at intervals of about three to five hours. The effectiveness of treatment extends for about eight hours after removal of the magnet or magnets. Relatively simple or minor ailments or complaints are cured with one or two hours of treatment.

Only relatively strong magnets should be utilized. The effectiveness and curative results increase with increase of power of the magnet applied to the extent the person can tolerate and withstand treatment.

The total magnetic flux applied to the patient is considered to be of key importance. The following formula sets forth the relationship between total flux, flux density and magnet pole area:
$\phi = BA$
Where: $\phi$=total flux
B=flux density in gauss
A=area Reference is made to the following text for explanation of relevant technology with respect to permanent magnets: *Permanent Magnet Design and Application Handbook,* Lester R. Moskowitz, Robert E. Krieger Publishing Company, Malabar, Fla., 1986.

As indicated earlier, only relatively strong magnets should be utilized.

The maximum power or total flux which should be applied may preferably be about 250,000 total flux. Such total flux is preferably measured at 0.001" from the north pole surface of the magnet means and such total flux relates to an average hand size of a person. Such total flux is the maximum power which is obtainable from the best grade permanent magnets commercially available under current technology. The power level used is normally between 100,000 to 250,000 total flux. An electromagnet of appropriate size for a hand or for an afflicted area can provide higher power if necessary or appropriate for particular treatment. It will be understood that the hand or hands of the person maintained in good contact with the north pole of the magnet means are accurate application of total flux, which as indicated above is measured at 0.001" from the magnet pole surface.

The range of magnetic power by total flux for applications to the hand and application to an afflicted area or spot, may typically be as follows:
Hand application: 100,000–250,000 total flux
Direct application to afflicted area: 5,000–250,000 total flux General guidelines for magnetic power levels in total flux found applicable for various ailments or applications are set forth in the table below:

| 1<br>Power Classification | Range of Power<br>(Total Flux 0.001"<br>from Magnet<br>Surface) | Typical Applications |
| --- | --- | --- |
| Low Power | 15,000 below | minor cut, light wound, headache, light pain |
| Medium Power | 15,000–100,000 | bruise, wound, cut, constipation, pain, ache, digestion, breathing, headache, stress, insomnia, and other light, simple, sickness |
| High Power | 100,000 above | all of the above, and chronic diseases and ailments |

If a cure or substantial alleviation is not achieved with the indirect method alone, then the combined indirect and direct method should be applied.

In applying magnets to both hands of a patient, it is desirable that magnets of equal size and power are applied to each hand and each side of the hand, palm or back.

Further particulars relative to magnets utilized with the invention are hereinafter outlined.

Typically, a flat magnet is employed, thus to provide substantially equal magnetic flux over the area of a hand or the afflicted body area. The magnet may have any configuration appropriate to the area to which it is to be applied, such as square, rectangular, circular or oval. The size of the magnet should be such as to cover the entire area of the hand including fingers or the afflicted area of the body, arm, leg, etc.

Strong magnets of relatively high power are preferred. Thus the magnets utilized are generally relatively thick and of substantial size, since the strength of a magnet is generally proportional to its size. Generally, the greater the power of the magnet, the greater the degree of cure effected by the magnet. However, magnets of substantially high power should not be utilized in treating infants, elderly persons, persons in a weakened or medically critical condition, those with serious illnesses or diseases, or pregnant women.

Permanent magnets are preferred for economic reasons, but electromagnets can be utilized to advantage because their power can be varied as desired, within design limitations.

The magnets may preferably be fabricated by powder metallurgy techniques, and may utilize such materials as cobalt iron and neodymium to provide high-power magnets.

The power or strength of a magnet also varies with the particular materials of which the magnet is fabricated and stronger cures are provided in accordance with increased curing or treatment effects. Therefore, the size of magnet to be utilized for a particular treatment, can vary widely. The appropriate magnet strength for particular ailments or diseases can be determined in accordance with the responses or reactions of the person and/or the afflicted portion of the body, by application of a particular magnet, then increasing the size of the magnet in accordance with the response of the patient.

The table below sets forth an appropriate magnet power classification in terms of size of permanent magnets:

| Power Classification | Thickness | Length | Width |
| --- | --- | --- | --- |
| Lower Power | ¼"–1" | 2"–6" | 2"–6" |
| Medium Power | 1"–2" | 2"–6" | 2"–6" |
| High Power | 2"–4" | 2"–6" | 2"–6" |
| Super High Power | 4" & Above | 6" & Above | 6" & Above |

In proceeding according to the invention, the afflicted area or spot is examined and a permanent magnet or electromagnet is selected for proper size and for provision of appropriate gauss or flux level. The person or patient is preferably in a prone position, as shown in FIG. 1, or seated position for the application of magnetism.

The direct treatment of an afflicted or diseased area involves application of a magnet directly to the afflicted area. The treatment time is typically one to two hours, typically twice daily. The north side of the magnet is applied directly to the afflicted spot or area and is left in place for one to two hours. Pain is typically then gone.

In utilizing the "direct" method in the combined method, a relatively wide bandage or belt may be applied or ensure good contact of the magnet with the body and skin of the patient at the afflicted spot or area. The maximum magnetic power or total flux which may preferably be applied to an afflicted area is about 250,000 total flux, as measured at 0.001" distance from the north magnetic pole surface. The size of magnet may typically be 4"×4" to 10"×10".

Treatment commences upon application of the magnet and typically extends from one to two hours, two times, per day, at intervals of about three to five hours. At the end of each treatment, the magnet or magnets are removed. The effectiveness of treatment extends about eight hours. Most ailments or diseases are cured or greatly alleviated with one or two treatments. Treatment may be repeated until complete cure is effected.

The patient may sense response involving complex symptoms, such as pain, strain, tightness, itch, warmth, coolness, etc. Such symptoms may be mixed and continue until the spot is cured or relieved.

The magnet may typically be applied for twenty to thirty minutes and for not more than two or three hours, in order to prevent undesirable side effects. After application of the magnet for an appropriate time, the patient senses a response and beneficial effects.

The direct method is effective for treatment of trauma, bruises, contusions, clearing of bruise discoloration, sprains and relatively simple pains or diseases. In treating such, the magnet is placed at the injury or afflicted site. The magnet is positioned so that it is not readily removable or separable from the skin of the patient in order to be properly effective. The magnet should be removed.

The direct method may preferably be utilized in repeated treatments in a continuous manner until relief and cure are affected. It may be used intermittently, but is effective only while the magnet is in contact with the person. It is therefore much preferred that the magnet be continuously applied. If a magnet is removed from contact before a proper treatment period, the previous period of application is ineffective and must be repeated.

The time period for treatment cannot be defined or described accurately, such range and time being dependent upon respective diseases and ailments, variations among individual persons, persons' conditions, past medical histories, environmental factors, individual characteristics, etc. Thus, for example, the range of time periods for headaches treatment can range from five to sixty minutes. The range of time periods for treatment of breathing difficulties may typically range from five to forty-five minutes. Such time durations for treatment are also dependent upon and are affected by factors including the power or total flux, and the size of the magnet means.

Thus there has been shown and described a novel treatment of afflictions and ailments with magnetism which fulfills all the objects and advantages sought therefor. Many changes, modifications, variations and other uses and applications of the subject invention will, however, become apparent to those skilled in the art after considering this specification together with the accompanying drawings and claims. All such changes, modifications, variations and other uses and applications which do not depart from the spirit and scope of the invention are deemed to be covered by the invention which is limited only by the claims which follow.

The inventor claims:

1. A method of treating and alleviating pains and inflammation of human afflictions by application of a north pole surface of a magnet to at least one hand of the body of a person being treated, the method comprising the steps of:

providing magnet means having at least one north pole surface adapted for application to said at least one hand, applying the north pole surface of the magnet means to said at least one hand and, maintaining the magnet in contact with said at least one hand for a period of from about 30 minutes to about 2 hours to heal and relieve pain, the total flux of the magnetic means applied to at least one hand being in the range from about 5000 $\phi$ to about 250,000 $\phi$.

2. The method according to claim 1 further including the step of:

repeating the application of the magnet means for at least one additional period of time.

3. A method according to claim 1, wherein: the magnet means are applied to both hands of the person.

4. A method according to claim 3, wherein:

separate respective magnet means of substantially equal total flux are applied to each respective hand of the person.

5. A method according to claim 3, and further including:

applying the magnet means alternately to one hand and to the other hand of the person for alternating time periods for balanced treatment.

6. A method according to claim 1, wherein substantially: the entire area of the palm or back of the hand of the person is fully covered by the north pole surface of the magnet means.

7. The method according to claim 1 wherein: the time period for treatment is repeated at least once in a 24 hour period in an interval of about 8 hours in accordance with treatment progress.

8. A method according to claim 1, and further including: disposing retaining means about the hand and the magnet means to provide effective contact of the magnet means north pole surface with the hand.

9. The method of claim 1 wherein said magnet means are applied to both hands of the person being treated and wherein the total flux of the magnet means applied to each hand is substantially equal.

10. The method of claim 1 wherein said magnet means are first applied to one hand of the person being treated and wherein said magnet means are then applied to the other hand of the person being treated.

11. The method of claim 10 wherein the total flux of the magnet means applied to each hand is substantially equal.

12. A method of treating and alleviating pains and afflictions of human ailments comprising the steps of:

applying the north pole surface of a magnet directly to a particular afflicted pain area of the body of a person being treated, said magnet having a size and shape to cover fully the afflicted pain area and having total flux of at least 5,000 $\phi$; and maintaining the magnet in contact with said body portion for a period of from about 30 minutes to about 2 hours.

* * * * *